(12) United States Patent  
Caroli et al.

(10) Patent No.: US 8,254,659 B2
(45) Date of Patent: Aug. 28, 2012

(54) METHOD AND APPARATUS FOR VISUALLY INSPECTING AN OBJECT

(75) Inventors: Sanzio Caroli, Castel San Pietro terme (IT); Donato Laico, Imola (IT)

(73) Assignee: Sacmi Cooperativa Meccanici Imolasocieta Cooperativa, Imola (IT)

( * ) Notice: Subject to any disclaimer, the term of this patent is extended or adjusted under 35 U.S.C. 154(b) by 1078 days.

(21) Appl. No.: 11/991,716

(22) PCT Filed: Sep. 9, 2005

(86) PCT No.: PCT/IB2005/002664
§ 371 (c)(1),
(2), (4) Date: May 14, 2008

(87) PCT Pub. No.: WO2007/029048
PCT Pub. Date: Mar. 15, 2007

(65) Prior Publication Data
US 2008/0310701 A1   Dec. 18, 2008

(51) Int. Cl.
*G06K 9/00* (2006.01)
(52) U.S. Cl. ........................ 382/141; 382/142
(58) Field of Classification Search .................. 382/141, 382/142
See application file for complete search history.

(56) References Cited

U.S. PATENT DOCUMENTS

| | | | |
|---|---|---|---|
| 5,659,626 A * | 8/1997 | Ort et al. ...................... | 382/125 |
| 6,100,990 A | 8/2000 | Ladewski et al. | |
| 6,239,870 B1 | 5/2001 | Heuft | |
| 6,424,414 B1 | 7/2002 | Weiland et al. | |
| 6,633,831 B2 * | 10/2003 | Nikoonahad et al. ......... | 702/155 |
| 7,102,750 B2 * | 9/2006 | Takami ......................... | 356/432 |
| 7,251,033 B1 * | 7/2007 | Phan et al. .................... | 356/432 |
| 7,463,367 B2 * | 12/2008 | Bowes .......................... | 356/604 |
| 7,577,278 B2 * | 8/2009 | Scholze ........................ | 382/124 |

FOREIGN PATENT DOCUMENTS

| | | |
|---|---|---|
| EP | 0 491 555 | 6/1992 |
| EP | 1 006 350 | 6/2000 |
| EP | 1 479 454 | 11/2004 |

OTHER PUBLICATIONS

International Search Report for PCT/IB2005/002664 mailed May 18, 2006.
Daugman, "Complete Discrete 2-D Gabor Transforms by Neural Networks for Image Analysis and Compression," (1988), pp. 1169-1179.

* cited by examiner

*Primary Examiner* — Tarifur Chowdhury
*Assistant Examiner* — Jonathan Hansen
(74) *Attorney, Agent, or Firm* — Nixon & Vanderhye P.C.

(57) ABSTRACT

A method comprises projecting a light and shade pattern defined by preset optic parameters through a body, detecting an image of the light and shade pattern through the body to obtain a detected image, processing the detected image to highlight any irregularities of the light and shade pattern in the detected image; an apparatus comprises a light-source for projecting a light and shade pattern defined by preset optic parameters through a body, an image-detecting device for detecting an image of the light and shade pattern through the body to obtain a detected image and a processing device for processing the detected image in such a way as to highlight any irregularities of the light and shade pattern in the detected image.

37 Claims, 8 Drawing Sheets

METHOD AND APPARATUS FOR VISUALLY INSPECTING AN OBJECT

CROSS-REFERENCE TO RELATED APPLICATIONS

This application is the U.S. national phase of International Application No. PCT/IB2005/002664, filed 9 Sep. 2005, which designated the U.S. The entire contents of that application is hereby incorporated by reference.

The invention relates to a method for visually inspecting an object, in particular made of in transparent plastics, for example a container, like a bottle, or a container preform, such a visual inspection enabling defects in the object to be identified.

The invention furthermore relates to an apparatus for visually inspecting an object.

EP0491555 discloses a method and an apparatus for inspecting a transparent object for detecting a defect. A pitch of stripes of a reference pattern is detected first. Then, an inspection object is placed in position and light having the reference pattern is projected upon the object to photograph transmission light by an image sensor. The picture element data thus obtained are stored into a memory and individually compared with a threshold value to determine the bright or the dark thereof. A threshold value is set from an average value between data of two picture elements spaced from each other by one half the pitch of the reference pattern. A defect of the object is discriminated from numbers of thus determined bright and dark picture elements.

U.S. Pat. No. 6,239,870 discloses a method for identifying defects in items made from transparent material, e.g. bottles. The items are inspected using a light source and a camera, a contrast pattern being arranged between the light source and the item to be inspected. Diffusely scattering defects are detected by a decrease in the contrast of the contrast pattern reproduced through the item.

U.S. Pat. No. 6,424,414 discloses a method and an apparatus for inspecting a transparent container for refractive defects that include positioning a light source in spaced relationship with respect to a detector which is operatively associated with a processor for receiving electrical signals from the detectors responsive to light passing through the container being received b the detector. The method includes positioning a grid filter having a plurality of alternating dark and light bands adjacent the light source so as to provide a multiple intensity gradient to the container. The container is positioned between the light source and the detector with the grid filter serving to provide adjacent alternate light and dark bands of light impinging on the container. Refractive defects cause a distortion of the intensity gradient received by the detector.

EP1006350 discloses a method for detecting defects in a barrel portion of a bottle. The defect in the barrel portion of the bottle includes a thin blister and a longitudinal streak. The defect in the bottle barrel is detected by imaging the bottle barrel with a CCD camera based on light which has passed through a light shield plate having a plurality of oblique slits and the bottle barrel, and processing the image of the bottle barrel generated by the CCD camera to determine whether or not the defect is present. Methods and apparatuses are known for detecting defects in a transparent object, for example a bottle or container preform, that provide a light source such as to illuminate the object and a light receiving device, for example a video camera, arranged in such a way as to receive the light that traverses the object, thus detecting an image of the object. From the comparison with the detected image and a sample image, for example of an object similar to the inspected object but free of defects, it is possible to establish whether and which defects are present in the inspected object.

A drawback of the known methods and apparatuses is that they enable only some types of defects to be identified that may be present in the object such as, for example, air bubbles, inclusions of foreign bodies, colour deviations and opaque zones. In fact, zones of the object at which one of the aforesaid defects is present absorb light in a different manner from further zones of the object that are free of such defects.

Other defects that do not significantly influence absorption of light by the object, such as for example surface deformation of the object, zones of the object having a different thickness from the prescribed thickness, zones of the object in which stress is concentrated inside the material of which the object is made, do not significantly influence light absorption, and cannot therefore be reliably detected by the methods and apparatuses mentioned above.

Apparatuses are furthermore known that enable defects to be detected that do not influence the absorption of light by a transparent object, such apparatuses providing a light polarising filter arranged between a light source and the object to be illuminated and a light receiving device, generally a video camera arranged opposite the light source, to detect an image of the object. The detected image has iridescent portions where there are defects, such as, for example, concentrations of stress.

Although the apparatuses that use polarised light enable defects to be detected that are due to stress or deformation of the material that forms the object, they require an operator to qualitatively analyse the detected image, such an analysis being substantially based on the experience and the skill of the aforementioned operator.

In other words, the images obtained with the use of polarised light are not suitable for being inspected automatically.

The aforementioned apparatuses cannot therefore be used to check defects in all the objects produced by a production line, but are useable only to carry out spot checks.

An object of the invention is to improve known methods and apparatuses to visually inspecting an object.

A further object is to obtain a method and apparatus that enable a wide range of defects to be detected in an object.

Another object is to obtain a method and apparatus for detecting defects in an object without the intervention of an operator being necessary.

Still another object is to obtain an apparatus for detecting defects in objects, which apparatus can be used for checking all the objects processed by a production or conveying line.

In a first aspect of the invention a method is provided comprising:
  projecting a light and shade pattern defined by preset optic parameters through a body;
  detecting an image of said light and shade pattern through said body to obtain a detected image;
  processing said detected image to highlight any irregularities of said light and shade pattern in said detected image.

In a second aspect of the invention an apparatus is provided comprising:
  a light-source for projecting a light and shade pattern defined by preset optic parameters through a body;
  an image-detecting device for detecting an image of said light and shade pattern through said body to obtain a detected image;
  a processing device for processing said detected image in such a way as to highlight any irregularities in said light and shade pattern in said detected image.

Owing to these aspects of the invention it is possible to obtain a method and apparatus that can effectively detect defects in an object.

Furthermore, the processed image is particularly suitable for being analysed automatically.

Figure 1:
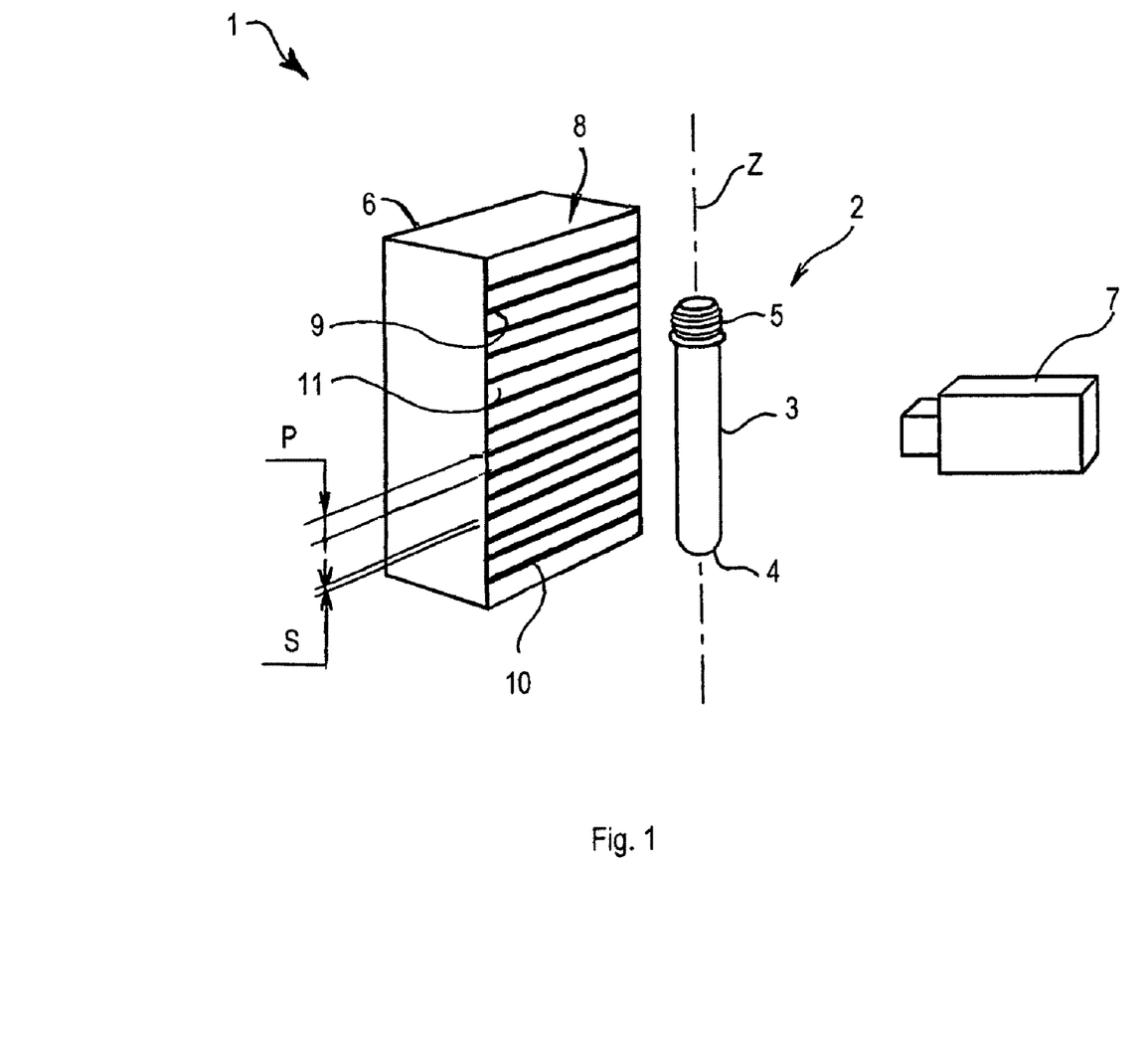
FIG. 1 is a schematic perspective view of a visual inspection device of an object, in particular a container preform.

The invention can be better understood and implemented with reference to the attached drawings that illustrate an embodiment thereof by way of non-limitative example, in which:

FIG. 1 shows a device 1 for visually inspecting an object, such as, for example, a preform 2 from which to obtain a container, in particular a bottle, in such a way as to identify any defects on the object.

The object to be inspected is made of material that is substantially transparent to visible light, such as glass, or, in the case of the preform 2, plastics, for example polyethyleneterephthalate (PET). The device 1 can also be used to inspect a container, in particular a bottle, this container being obtainable from the preform 2 by stretch-blow moulding.

The preform 2 comprises a substantially cylindrical body 3, that extends along a longitudinal axis Z and is closed at a first end 4 by a curved wall and open at a second end 5, in which protrusions are provided that are suitable for defining a thread of a neck of a container.

The device 1 comprises a light source, in particular an illuminating device 6, preferably comprising an emitting surface, for example a surface that emits light in an equal and uniform manner at each portion of the aforementioned surface.

The illuminating device 6 is arranged for illuminating the body 3 of the preform 2.

The device 1 furthermore comprises a light receiving device, for example a camera or a video camera 7, arranged in such a way as to receive the light that traverses the preform 2, thus detecting an image of the preform 2.

Between the illuminating device 6 and the preform 2 a grid 8 is provided that comprises a grid-shaped pattern 9, provided with a plurality of stripes 10 that are substantially parallel to one another. The grid 8 is arranged in such a way that the stripes 10 are substantially orthogonal to the longitudinal axis Z.

Each stripe 10 comprises a band that is substantially not transparent to the light emitted by the illuminating device 6, for example black in colour, having thickness S, measured in a direction that is orthogonal to an extension direction of the stripe 10, i.e. parallel to the longitudinal axis Z. The stripes 10 have the same thicknesses S and are arranged in a substantially constant pitch P.

The grid 8 is obtained on an emission surface 11 of the illuminating device 6, this emission surface 11 being arranged for directing outside the illuminating device 6 the light produced by the light source. The grid-shaped pattern 9 can be arranged by printing a striped pattern on the emission surface 11, for example according to a known silkscreen-printing technique.

In other words, the illuminating device 6 cooperates with the grid 8 to project a light and shade pattern defined by preset optic parameters—the thickness S and the pitch P—through the body 3.

In a embodiment that is not shown, the grid 8 is distinct from the illuminating device 6 and is distanced from it.

The video camera 7 detects an image of the grid-shaped pattern 9 projected from the illuminating device 6 through the preform 2.

Figure 4:
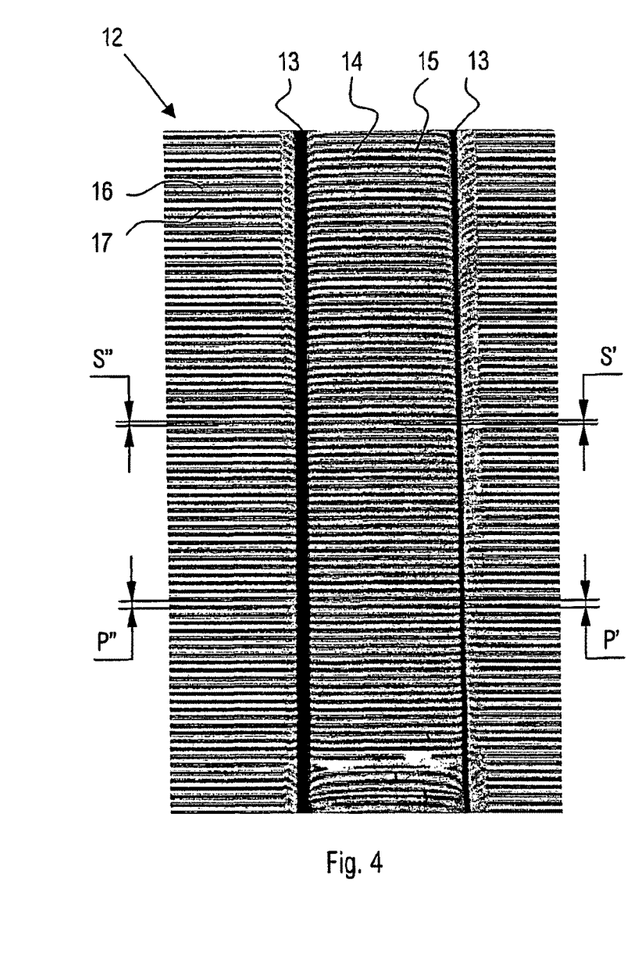
FIG. 4 is an image of a container preform detected by the device in FIG. 1.

In FIG. 4, a first image 12 of a preform 2 is shown that is free of defects, as detected by the device 1.

The first image 12 comprises two black vertical lines 13, corresponding to edges of a profile of the body 3, and a plurality of white lines 14 that alternate with a plurality of black lines 15, that define the detected light and shade pattern. The white lines 14 and the black lines 15 are parallel to one another and substantially orthogonal to the two black vertical lines 13, i.e. to the longitudinal axis Z. Outside the two black vertical lines 13 a further plurality of white lines 16 and a further plurality of black lines 17 are present, the white lines 16 the and black lines 17, alternating, being arranged parallel to one another and substantially orthogonally to the two black vertical lines 13.

The plurality of black lines 15 defines an image of the stripes 10 that is detected through a cylindrical lens formed by the body 3 and the further plurality of black lines 17 defines an image of the stripes 10 that is detected outside the body 3, i.e. by detecting rays of light that traverse the grid 8 but do not traverse the preform 2.

Each black line of the plurality of black lines 15 has a thickness S' that is substantially the same for all the black lines of the plurality of black lines 15, which are distributed according to a substantially constant pitch P'.

Similarly, each further black line of the further plurality of black lines 17 has a thickness S" that is substantially the same as for all the further black lines of the further plurality of black lines 17, these further black lines being arranged according to a substantially constant pitch P'".

The thicknesses S' and S" are substantially the same as one another and the pitches P' and P" are substantially the same as one another. Furthermore, the thicknesses S' and S" are substantially the same as the thickness S and the pitches P' and P'" are substantially the same as the pitch P.

The body 3 that is free of defects thus acts substantially like a theoretical lens.

An advantage of the grid-shaped pattern 9—i.e. with stripes 10 substantially orthogonal to the longitudinal axis Z of the body 3—is that the cylindrical lens defined by a body 3 free of defects enables an image of the stripes 10 to be obtained that is substantially the same as an image of the stripes 10 detected without interposing between the grid 8 and the video camera 7 the cylindrical lens defined by the body 3.

The body 3, if free of defects, does not therefore deform the appearance of the stripes 10, i.e. transforms the grid-shaped pattern 9 into an image comprising a plurality of lines having dimensional and distribution features that are substantially the same as those of the grid-shaped pattern 9. When the preform 2 comprises on the other hand defects, such as, for example deformation of the surface of the body 3, zones of the body 3 having a different thickness in relation to a set thickness, zones of the body 3 in which stress is concentrated inside the material of which the preform 2 is made, the cylindrical lens defined by the body 3 deforms the appearance of the stripes 10 at the points at which the defects are present.

Figure 5:
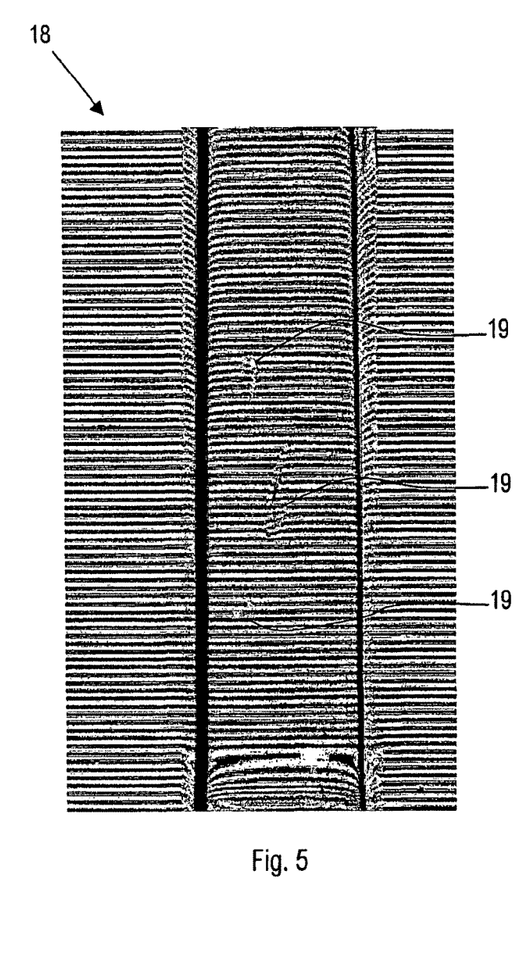
FIG. 5 is an image like the one in FIG. 4 relating to a further container preform.

FIG. 5 shows a second image 18 of a preform 2 that comprises defects of the aforementioned types.

The body 3, in the zones in which defects are present, operates like a lens that is different from a theoretical lens and the image of the grid-shaped pattern 9 no longer corresponds to a plurality of substantially parallel lines having a substantially constant thickness and being substantially mutually equidistant. In fact, in the second image 18 distortion zones 19 are identifiable in which the plurality of lines is irregular and distorted. Such distortion zones 19 show the presence of defects in the preform 2.

In order to visually inspect the preform 2, the preform 2 is arranged in a reference position opposite the grid 8, in which the longitudinal axis Z is substantially orthogonal to the stripes 10.

The video camera 7 is connected to an image-processing device, for example a computer, that is not shown, in which a processing algorithm is implemented that enables the detected images to be transformed in processed images in such a way as to highlight any irregularities in the light and shade pattern that may be present in the detected image.

Figure 6:
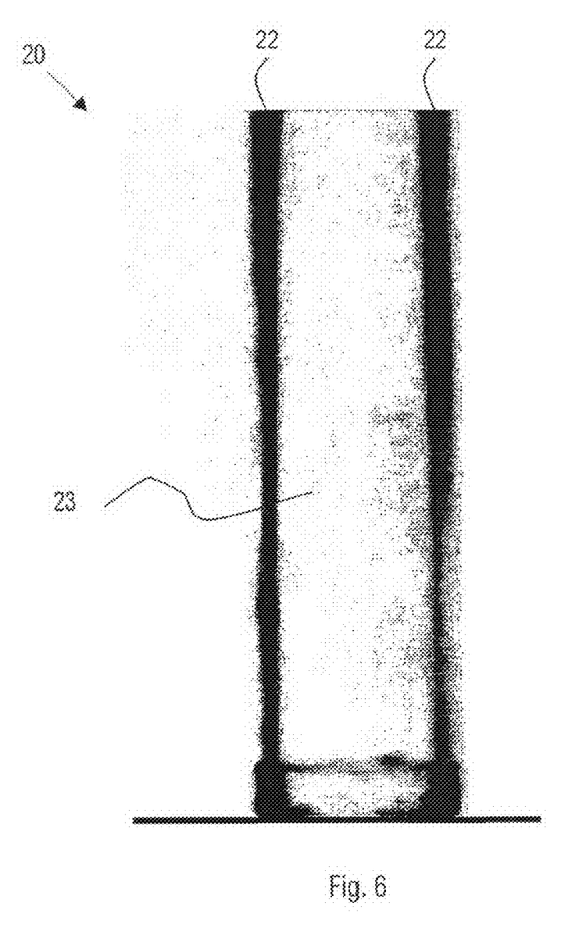
FIG. 6 is an image resulting from the processing of the image of FIG. 4, the processing being conducted by the device in FIG. 1.
Figure 7:
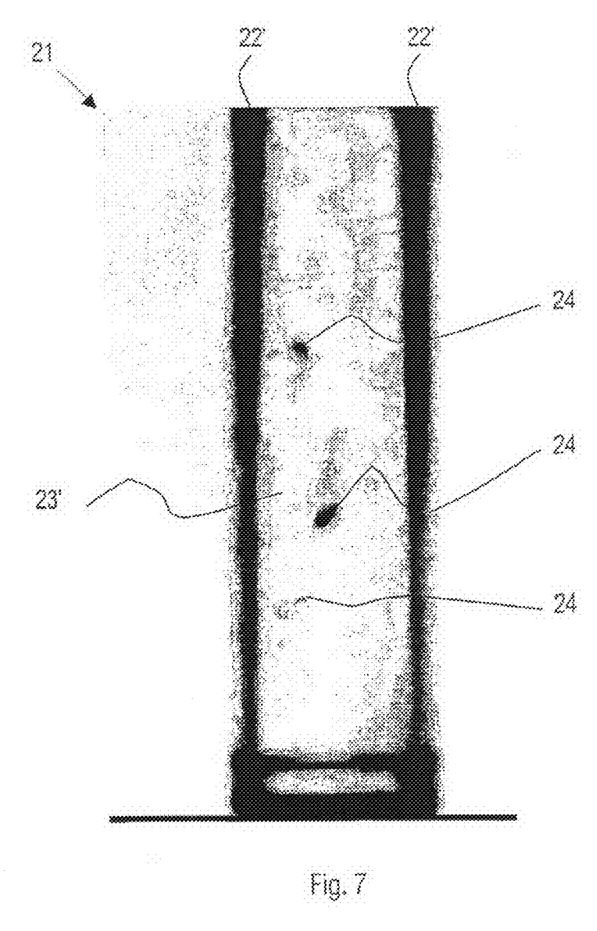
FIG. 7 is an image like the one in FIG. 6 and arising from processing of the image in FIG. 5.

The detected image, for example the first image 12 or the second image 18, is filtered by the processing algorithm in such a way as to delete the plurality of black lines 15 and the further plurality of black lines 17, so as to obtain from the first image 12 a first processed image 20, shown in FIG. 6, and from the second image 18 a second processed image 21, shown in FIG. 7.

The first processed image 20 and the second processed image 21 respectively comprise a pair of black vertical lines 22, 22', between which a region with a substantially uniform colour 23, 23' is interposed, this pair of black vertical lines 22, 22' corresponding to the two black vertical lines 13 of the detected image, i.e. of the first image 12 and of the second image 18, respectively. The second processed image 21 furthermore comprises, in the region with a substantially uniform colour 23', portions 24 having a colour that is distinct from a background colour of the region with a substantially uniform colour 23'. These portions 24 correspond, in shape and size, to the distortion zones 19 of the second image 18 detected by the video camera 7.

In the first processed image 20, these portions 24 are not present inasmuch as the processed image is associated with a preform 2 that is free of defects.

The effect that is obtained by deleting the image of the grid-shaped pattern 9 from the detected image is thus that of obtaining a processed image in which the defects in the body 3 of the preform 2 are highlighted in the form of specks.

In the image-processing device defect-recognition algorithms can also be implemented that analyse the processed image 20, 21.

For example, one of these algorithms comprises a blob-analysis technique ("blob analysis") that is based on an analysis of pixels that form an image and that enables dimensional and distribution features of the specks to be obtained and the identified specks to be classified, i.e. the type of defect associated with a speck to be classified.

Alternatively, the processed images can be analysed by a technique that analyses a histogram of the image, or by comparison of an image with a sample image.

The image-processing device, in addition to filtering the detected image, is thus able to establish whether defects are present in a preform 2 and to classify the type of detected defect.

The image-processing device can also make a comparison between the processed image and a sample image stored in a memory unit of the image-processing device and thus establish whether the preform 2 inspected can be considered to conform to a preset quality level.

Alternatively, an analysing device, distinct from the image-processing device but connected to it, comprises the defect-recognition algorithm and carries out the analysis of the processed image and identifies whether the processed image conforms to the sample image, i.e. if the preform 2 conforms to the prescribed level of quality.

Owing to the device 1 it is thus possible to visually inspecting the defects present in an object without the intervention of an operator being required to analyse the detected images and decide which are the objects that cannot be processed in subsequent processing steps, as occurs in prior-art apparatuses.

The device 1 can therefore be used to carry out an inspection of a plurality of objects processed on a line of a system. In particular, it is possible to inspect all the objects conveyed along a production and/or working line.

In an alternative embodiment, the image-processing device may not comprise the defect-recognition algorithm or may not be provided with an analysing device distinct from the image-processing device. In this case, an operator examines the image processed by the image-processing device and identifies, on the basis of a comparison between the processed image an a sample image, the preforms that do not conform to the preset level of quality.

Owing to the image-processing device, and in particular to the processing algorithm, the processed images are easier to read also for the naked eye, i.e. it is easier to identify any differences between the processed image and the sample image, compared with cases in which iridescent images have to be analysed that are obtained with the known techniques that use polarised light. Consequently, the outcome of the inspection conducted by the operator of the processed image is less subject to the personal skill of the operator.

Naturally, the colours of the detected image, like those of the processed image, may be different from black and white as disclosed above. Images that are easier for both the computer and/or the analysing device and the operator to read can be obtained by choosing two colours that strongly contrast with each other.

The image-processing device can use a filtering technique that involves the use of Gabor filters.

For a detailed account of the Gabor filter the documents listed below can be consulted:

Gabor, D. (1946); Theory of Communication; J. Inst. Elec. Eng. 93, 429-441;

J. Daughman; "Complete discrete 2-D Gabor Transform by neural networks for image analysis and compression"; IEEE trans., Acoustic, Speech, Signal Proc., vol. 35, n.7, pp. 1169-1179, 1988.

The Gabor filter is substantially a Gaussian filter (with sx variance and sy variance along the x and y axes respectively) modulated by a complex sinusoid (with central frequencies U and V along the axis x and y respectively) described by the following equations:

$$G_{real}(x, y, \vartheta, f) = e^{\left(-\frac{1}{2}\left\{\left(\frac{x'}{sx'}\right)^2 + \left(\frac{y'}{sy'}\right)^2\right\}\right)} \cdot \cos(2 \cdot \pi \cdot f \cdot x')$$

$$G_{imm}(x, y, \vartheta, f) = e^{\left(-\frac{1}{2}\left\{\left(\frac{x'}{sx'}\right)^2 + \left(\frac{y'}{sy'}\right)^2\right\}\right)} \cdot \sin(2 \cdot \pi \cdot f \cdot x')$$

where $x' = x \cdot \cos(\theta) + y \cdot \sin(\theta)$ $y' = y \cdot \cos(\theta) - x \cdot \sin(\theta)$ being sx' and sy': the variance along the x and y axis respectively;
f: the frequency of the sinusoid function (corresponding to the frequency of the lines of the grid-shaped pattern θ);
θ: the orientation of the Gabor filter (equal to 0 inasmuch as the lines of the grid-shaped pattern 9 are horizontal).

By acquiring an image of only the grid-shaped pattern 9 it is possible to calculate the period—i.e. the reciprocal of the frequency f—of the grid-shaped pattern 9 (as the average of the distance between the black lines) and the variance, defined here below:

if Si{1 ... N} are the distances between the black lines where N+1 is the number of the lines contained in the image, the period is:

$$\overline{S} = \sum_{i=1}^{n} \frac{Si}{N}$$

and the variance:

$$\text{Var}S = \frac{\sum_{i=1}^{n}(Si - \overline{S})^2}{N}$$

The dimension of the kernel of the filter is calculated so that it comprises 99.8% of the Gaussian envelope in all directions.

In the application in FIGS. 4 and 5 the period of the grid is 5.81 pixels, the value of the variances is 15.04 and the dimension of the filter is 29×29 pixels. The filter equations become:

$$G_{real}(x, y) = e^{\left(-\frac{1}{2}\left\{\left(\frac{x}{15.04}\right)^2 + \left(\frac{y}{15.04}\right)^2\right\}\right)} \cdot \cos(1.08 \cdot x)$$

$$G_{imm}(x, y) = e^{\left(-\frac{1}{2}\left\{\left(\frac{x}{15.04}\right)^2 + \left(\frac{y}{15.04}\right)^2\right\}\right)} \cdot \sin(1.08 \cdot x)$$

Figure 10:
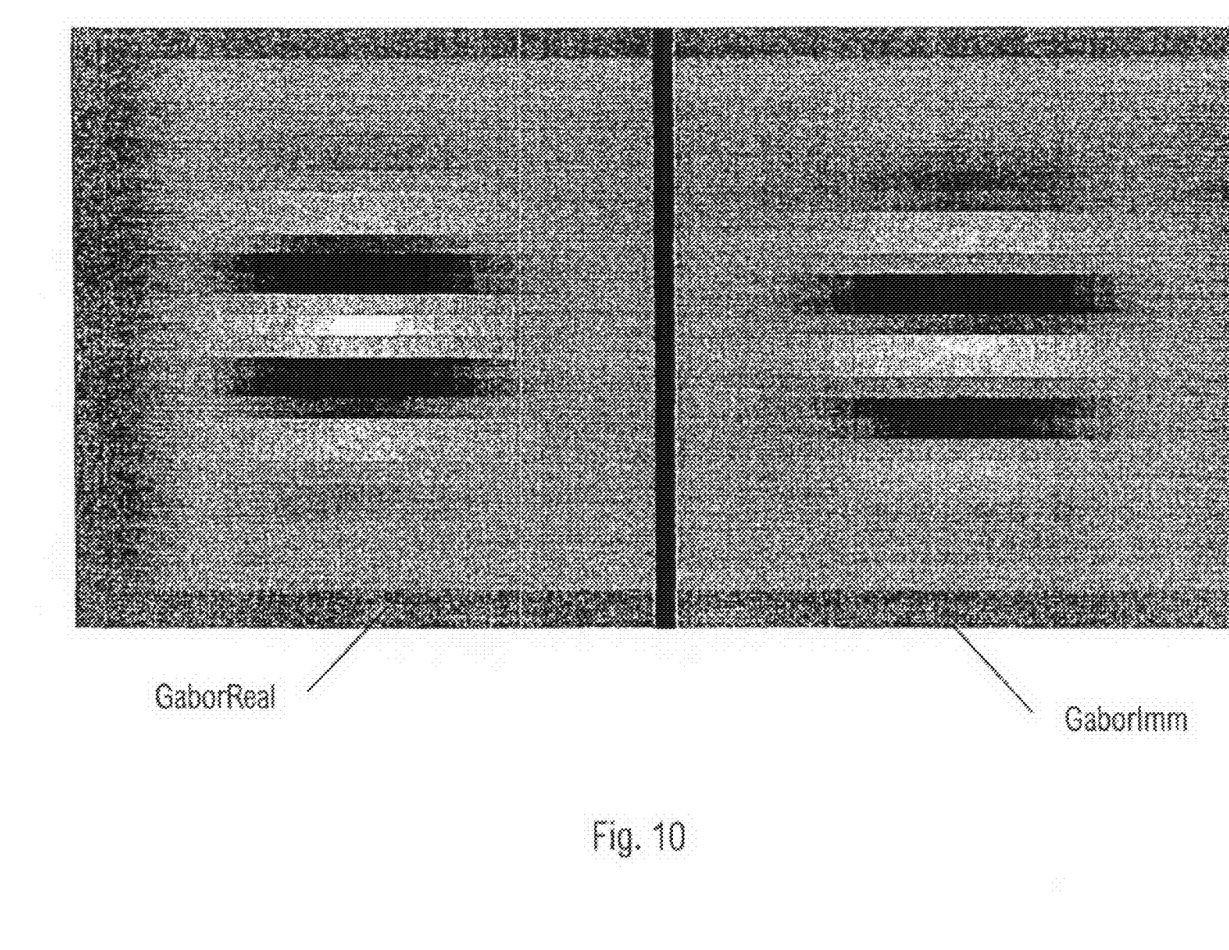
FIG. 10 is an image of the real part and of the imaginary part of a Gabor filter made according to the method disclosed by the flow-chart in FIG. 8 and used in the method disclosed by the flow-chart in FIG. 9.

FIG. 10 shows the images of the real part GaborReal and of the imaginary part GaborImm of the Gabor filter the equations of which are set out above.

The Gabor filter is constructed by knowing the thickness S and the pitch P of the stripes 10 of the grid-shaped pattern 9.

The Gabor filter eliminates the image of the grid 9 at the points in which the plurality of black lines 15 is regular and shows the defects with specks, generally black in colour, at the points in which the distortion zones 19 are present. The combination of the Gabor with the particular grid-shaped pattern 9 is rather advantageous inasmuch as the image of the grid-shaped pattern 9, namely the plurality of black lines 15, does not undergo deformation when there are no deformation defects in the preform 2 and when the preform 2 moves little from the reference position, i.e. if the longitudinal axis Z is slightly tilted in relation to a preset plane.

An advantage of the grid-shaped pattern 9 is that if the preform 2 has a position that is little different from the reference position, the detected image does not undergo substantial variation in relation to an image of the preform obtained with the preform 2 located in the reference position. This means that the device 1 is not affected, within a certain limit—by possible variations of the position of the preform 2.

Patterns of the grid 8 that are different from the grid-shaped pattern 9 supply through the cylindrical lens defined by the body 3, if free of defects, an image that is significantly affected by possible shifts of the preform 2 from the reference position.

For example, if the grid 8 comprises a vertical striped pattern—i.e. with stripes parallel to the longitudinal axis Z—the stripes having a constant thickness and being equidistant from one another, the body 3, if free of defects, transforms the aforesaid pattern into an image comprising two black vertical lines, corresponding to edges of the preform 2, and central vertical lines interposed between the two black vertical lines, having a greater distance from each other than further vertical lines arranged near the two black vertical lines. The detected image is thus rather different from the equal and equidistant vertical striped pattern. In this case, if the preform 2 were not located correctly in the reference position, an image of the grid 8 through the body 3 that was different for each position reached by the preform 2 would be obtained.

As a result, it would not be possible to use the same filter systematically for the detected images of all the inspected preforms, but it would be necessary to again calculate the filter parameters for each analysed preform and for each preform position that was different from the reference position. The processing algorithm would be rather complex and difficult to manage. Furthermore, the outcome of the visual inspection would not be sufficiently reliable.

The processing algorithm and the defect-recognition algorithm enable operation according to the following steps: a first step in which the Gabor filter is defined, a second step in which the image detected by the video camera 7 is processed by the Gabor filter and the image that is thus processed that arises from filtering is analysed by a known image-analysis technique such as, for example, a comparison of the processed image with a sample image, or analysis of the histogram of the processed image, or segmentation of the image and blob analysis. The analysis of the processed image enables any non-uniform zones of the processed image to be recognised in such a way as to define whether the inspected preform conforms or does not conform to a desired qualitative level.

In an embodiment, the first step furthermore provides for storing of a sequence of images of preforms that are free of defects from which it is possible to obtain statistical information that is significant for subsequent detection of defects. In this embodiment, during the second step a processed image is compared with the statistical information acquired in the first step.

Figure 8:
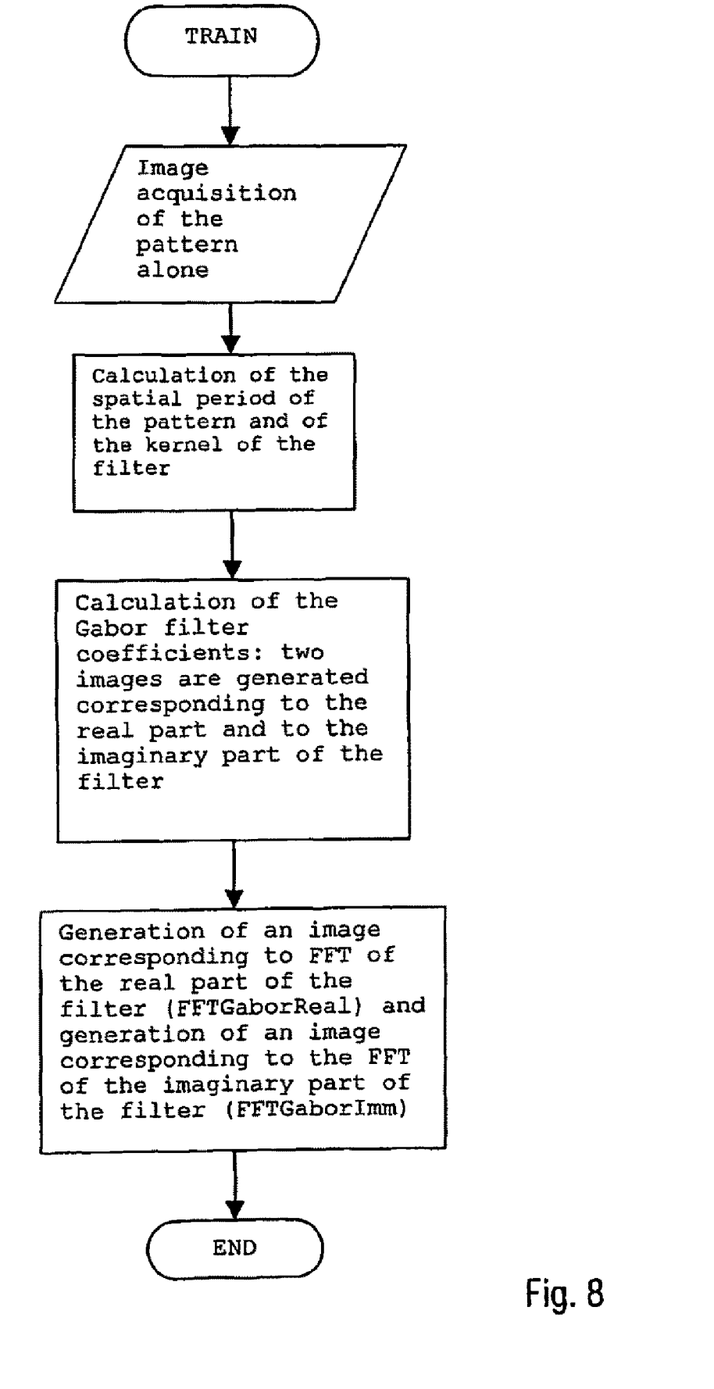
FIG. 8 is a flow-chart illustrating a method for obtaining a filter for processing an image.

FIG. 8 illustrates a flow-chart in which a sequence of procedures is indicated that can be comprised in the first step—also called "train". The first step is run for a first and only time, in such a way as to define the filter, which, depending on the thickness S and on the pitch P of the grid-shaped pattern 9, is subsequently used to process all the detected images.

This enables an algorithm to be obtained having low complexity, in particular if compared with algorithms that require the filter parameters to be calculated for each object to be inspected.

The first step provides for acquiring an image of the grid 8, i.e. of the grid-shaped pattern 9, without any preform 2 being interposed between the grid 8 and the video camera 7.

The detected image is interpreted as a matrix. Subsequently, the spatial period of the pattern is calculated, i.e. the thickness S and the pitch P, and the coefficients that define a filter operator is calculated, being the total of these coefficients also called "kernel" of the filter. The coefficients of the Gabor filter are then calculated, which comprises a real part and an imaginary part, i.e. coefficients of two matrices corresponding respectively to the real part and to the imaginary part of the Gabor filter are calculated. Lastly, the fast Fourier transforms (FFTs) are calculated both for the imaginary part of the filter and for the real part of the filter and, from the fast Fourier transforms, an image is obtained corresponding to the fast Fourier transform of the real part of the filter (FFTGaborReal) and an image is obtained corresponding to the fast Fourier transform of the imaginary part of the filter (FFTGaborImm).

At this point, the filter operator is defined and can be applied to images detected by the video camera 7.

Figure 9:
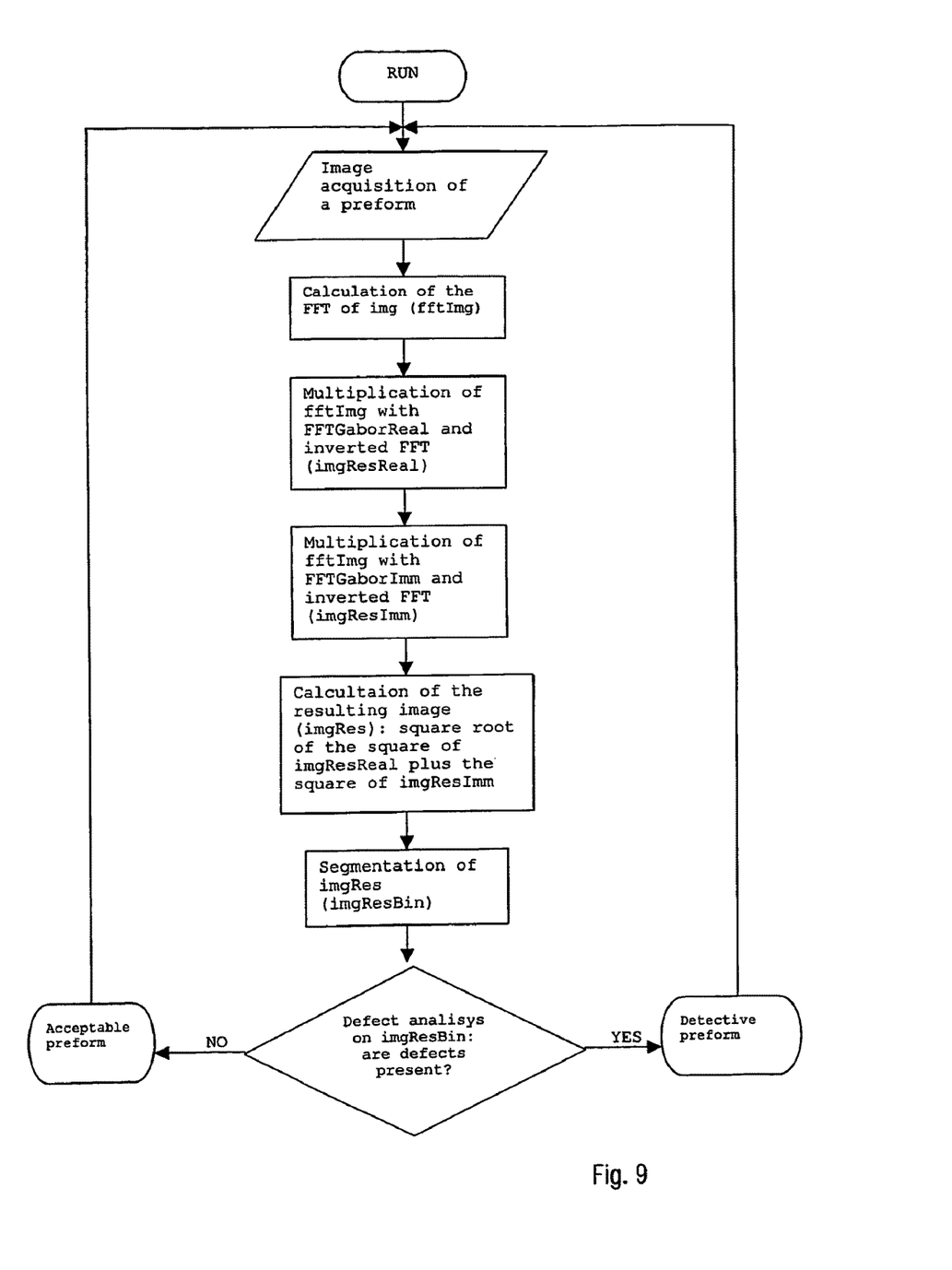
FIG. 9 is a flow-chart illustrating a method for processing an image detected by the device in FIG. 1.

FIG. 9 shows a flow-chart that summarises an image-processing procedure, also called "run", which is carried out on each image acquired by the video camera 7. Initially, an image (img) of a preform 2 is acquired, by interpreting the image as a matrix. The fast Fourier transform of the detected image (fftImg) is then calculated. The fast Fourier transform of the detected image (fftImg) is multiplied by the fast Fourier transform of the real part of the filter (FFTGaborReal) and the antitransform (inverted FFT) of the resulting product is calculated so as the real part of the resulting image (imgResReal) is obtained. Similarly, the fast Fourier transform of the detected image (fftImg) is multiplied by the fast Fourier transform of the imaginary part of the filter (FFTGaborImm) and the antitransform (inverted FFT) of the resulting product is calculated so as an imaginary part of the resulting image (imgResImm) is obtained.

The multiplication between the fast Fourier transform of the detected image (fftImg) and the fast Fourier transform of the real part of the filter (FFTGaborReal) and the subsequent antitransform, and the multiplication between the fast Fourier transform of the detected image (fftImg) and the fast Fourier transform of the imaginary part of the filter (FFTGaborImm) and the subsequent antitransform enable the method to be simplified inasmuch as they avoid to calculate the convolution product.

The resulting processing image (imgRes) is obtained by calculation of the square root of the sum of the squares of the real part of the image and of the imaginary part of the image.

Subsequently, the resulting image (imgRes) is analysed by prior-art image-analysis, for example by segmentation of the resulting image (imgRes). Segmentation provides an image (imgResBin) on the basis of which it is established whether the inspected preform is to be considered to be acceptable, i.e. substantially conforming to the desired quality requirements, or is to be considered to be defective and therefore no longer processable.

Alternatively, it is possible to calculate the Fourier transforms of the aforementioned functions rather than calculate the fast Fourier transforms. Calculating the fast Fourier transforms enables the method disclosed above to be simplified.

Figure 2:
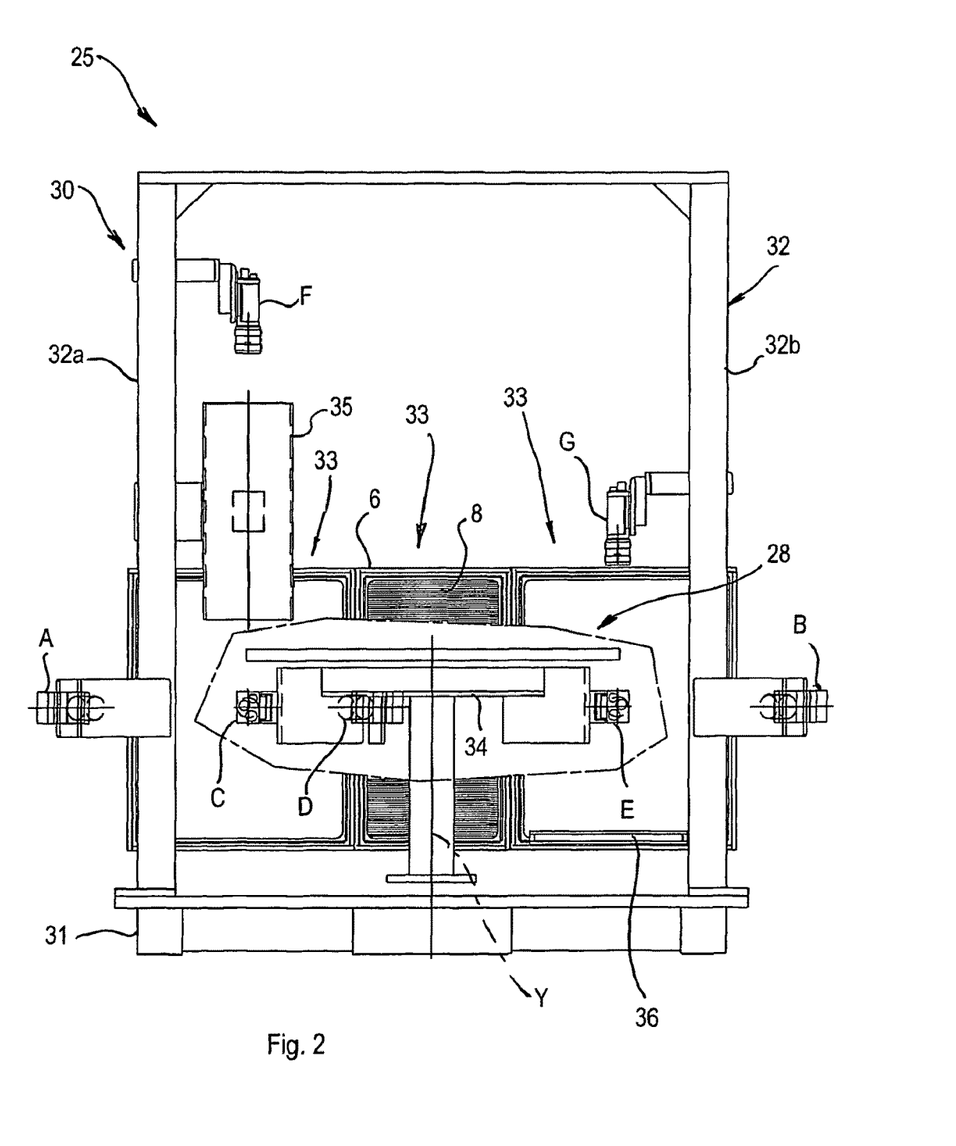
FIG. 2 is a partially sectioned frontal view, illustrating an apparatus provided with the device in FIG. 1.
Figure 3:
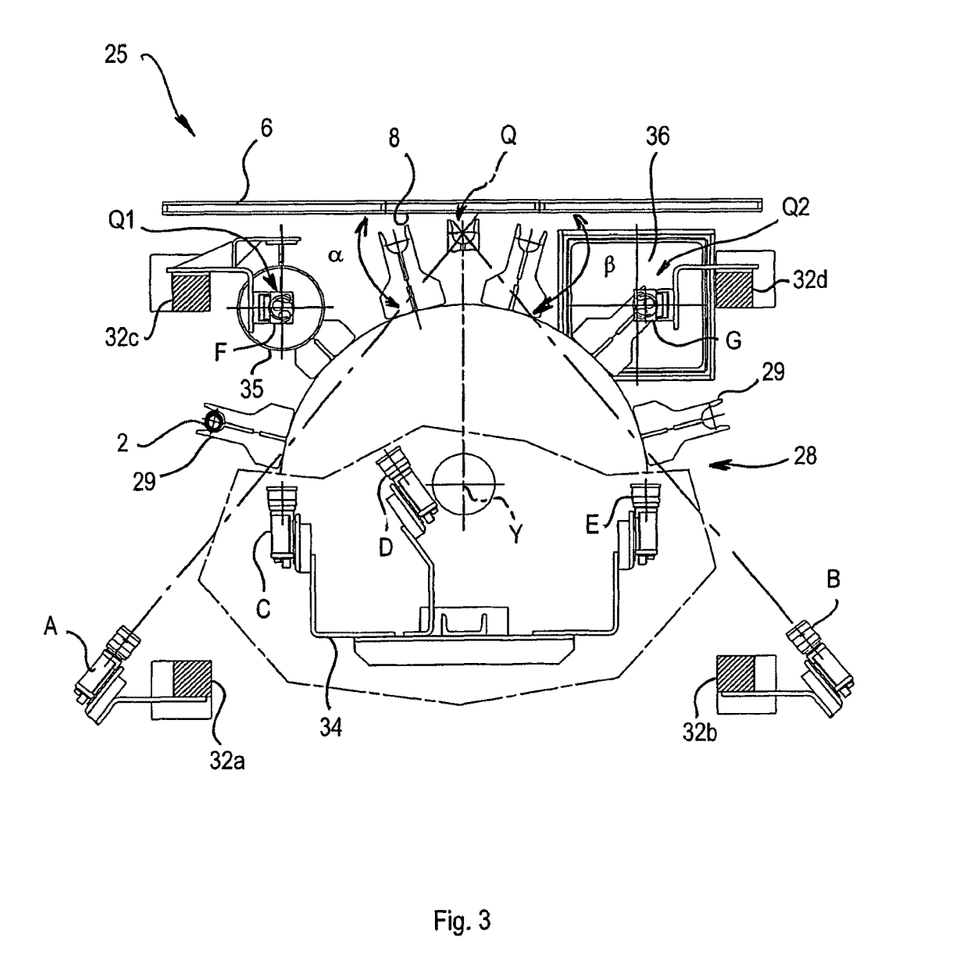
FIG. 3 is a partially sectioned plan view of the apparatus in FIG. 2.

FIGS. 2 and 3 show an apparatus 25 provided with a device 1 for the visual inspection of a preform 2 of the type disclosed above. The apparatus 25 in fact comprises an illuminating device 6 provided with a grid 8, which comprises a grid-shaped pattern 9 of the type disclosed above, to which a preform 2 is periodically faced. The apparatus 25 comprises a carousel 28 that is rotatable around a substantially vertical axis Y and is provided with grippers 29 associated with an edge zone of the carousel 28 according to a substantially constant angular pitch. The grippers 29 are suitable for interacting with the second end 5 of each preform 2 to support the preform 2 and convey it from a removing position that is not shown, through inspection positions of the preform 2, in which the preform 2 is subjected to visual inspection, to a delivery position, in which the preform 2 is delivered to another apparatus or is deposited in a collecting container.

The grippers 29 are shaped in such a way that the longitudinal axis Z of the preforms 2 is substantially parallel to the axis Y and substantially perpendicular to the stripes 10 of the grid-shaped pattern 9.

The apparatus 25 is provided with a frame 30 comprising a base 31 with a substantially square shape and uprights 32 arranged near vertexes of the base 31. The carousel 28 is assembled in a central zone of the base 31.

The illuminating device 6 comprises three illuminating surfaces 33 assembled substantially parallel to two uprights 32c, 32d, of the frame 30 and near the base 31 in such a way that the preforms 2, in each inspection position, face a central portion of at least an illuminating surface of the three illuminating surfaces 33. The grid 8 is obtained on one of the illuminating surfaces 33, in particular on a central illuminating surface interposed between the other two.

The apparatus 25 comprises a first video camera A arranged opposite the illuminating device 6 in relation to the carousel 28 to detect an image of a preform 2 in a reference position Q, the reference position Q being provided opposite the grid 8 and near the latter. The first video camera A is fixed to a first upright 32a arranged on a side of the base 31 that is more distant from the illuminating device 6. The first video camera A is tilted by a first angle $\alpha$, which is an acute angle, in relation to a plane containing the three illuminating surfaces 33.

The apparatus 25 furthermore comprises a second video camera B arranged opposite the illuminating device 6 in relation to the carousel 28 to detect an image of a preform 2 in the reference position Q. The second video camera B is fixed to a second upright 32b and is tilted by a second angle $\beta$, which is an acute angle, in relation to the plane containing the three illuminating surfaces 33.

In a embodiment, the first angle $\alpha$ and the second angle $\beta$ are substantially equal to each other, in such a way that the first video camera A and the second video camera B are substantially symmetrical to a plane passing through the Y axis and the reference position Q.

Using the first video camera A and the second video camera B, arranged in such a way as to interact simultaneously with a preform 2 in the reference position Q, enables a significant portion of the body 3 of the preform 2 to be inspected.

The first video camera A and the second video camera B are comprised in the system of visual inspection of the device 1 and are therefore connected to an image-processing device that is not shown that enables to detect whether preforms 2 comprise defects such as surface deformation, thickness differing from the prescribed thickness, or concentration of stress.

The apparatus 25 furthermore comprises further video cameras for also detecting other types of defects, for example air bubbles, inclusions of foreign bodies, colour deviations, opaque zones. In particular, a third video camera C and a fourth video camera D are provided that are suitable for inspecting the body 3 of the preform 2 when it is positioned in a first position Q1, near a third upright 32c, and a fifth video camera E that is suitable for inspecting the body 3 when the preform 2 is located in a second position Q2 near a fourth upright 32d.

The video cameras C, D and E are fitted to a support 34 arranged below the carousel 28.

The apparatus 25 comprises a sixth video camera F, arranged for inspecting the second end 5 of the preform 2, when the preform 2 is in the first position Q1, so as to check whether the protrusions of the second end 5 are complete, whether there are flaws or flushes or whether the second end 5 is cylindrical or oval. The sixth video camera F is assembled on the third upright 32c above the first position Q1 with the lens facing the first position Q1. Between the sixth video camera F and the position Q1 a further illuminating device 35 is interposed that illuminates the second end 5.

In fact, the apparatus 25 comprises a seventh video camera G arranged for inspecting the first end 4 of the preform 2, when the preform 2 is in the second position Q2, so as to identify any flashes on the bottom of the body 3, inclusions of foreign bodies, specks, points at which crystallisation of the plastics has occurred, holes at the injection points. The seventh video camera G is fixed on the fourth upright 32d above the second position Q2 with the lens facing that position.

The apparatus 25 furthermore comprises a still further illuminating device 36 positioned in such a way that the preform 2, when it is in the second position Q2, is interposed between the seventh video camera G and the further illuminating device 36.

The apparatus 25 thus enables a wide range of defects that may occur in the preforms 2 to be identified and analysed.

The invention claimed is:

1. Method comprising:
providing a light source;
providing an image detecting device;
providing a grid having, a plurality of parallel stripes;
providing a body, said body having a cylindrical symmetry and a longitudinal axis, said body being arranged between said grid and said image detecting device, and said grid being arranged between said light source and said body, and in such way that said longitudinal axis is orthogonal with respect to said stripes of said grid;
projecting a light and shade pattern obtained by said grid and defined by preset optic parameters through said body, said light and shade pattern comprising a striped pattern which in its turn comprises stripes that are substantially orthogonal to the longitudinal axis of said body;
detecting by said image detecting device an image of said light and shade pattern through said body to obtain a detected image, so that said detected image comprises a plurality of lines, said lines being substantially orthogonal to said longitudinal axis;
processing said detected image to highlight any irregularities of said light and shade pattern in said detected image, said processing comprising filtering by means of a Gabor filter said detected image to obtain a processed image.

2. Method according to claim 1, wherein said filtering comprises deleting from said detected image a further image of said light and shade pattern, being provided detecting said light and shade pattern in the absence of said body to obtain said further image.

3. Method according to claim 2, wherein said detected image comprises a plurality of lines, said lines of said plurality of lines being substantially orthogonal to a longitudinal axis of said body and said further image comprises a further plurality of lines said lines of said further plurality of lines being substantially orthogonal to said longitudinal axis.

4. Method according to claim 1, wherein said Gabor filter comprises a real part and an imaginary part.

5. Method according to claim 4, wherein said processing comprises calculating the Fourier transform of said detected image.

6. Method according to claim 5, wherein said processing further comprises calculating the Fourier transform of said real part.

7. Method according to claim 6, wherein said processing comprises multiplying said Fourier transform of said detected image by said Fourier transform of said real part to obtain a product.

8. Method according to claim 7, wherein said processing comprises calculating the antitransform of said product to obtain a real part of said processed image.

9. Method according to claim 7, wherein said processing further comprises calculating the Fourier transform of said imaginary part.

10. Method according to claim 9, wherein said processing comprises multiplying said Fourier transform of said detected image by said Fourier transform of said imaginary part to obtain a further product.

11. Method according to claim 10, wherein said processing comprises calculating the antitransform of said further product to obtain an imaginary part of said processed image.

12. Method according to claim 11, wherein said processing comprises extracting the square root of the sum of the squares of said real part of said processed image and of said imaginary part of said processed image to obtain a resulting image.

13. Method according to claim 12, and further comprising analyzing said resulting image.

14. Method according to claim 13, wherein said analysing comprises applying an image-analysis technique provided in a group of said segmented image, analysing a histogram of said resulting image, comparing said resulting image with a sample image.

15. Method according to claim 14, and further comprising classifying said body on the basis of the outcome of said analysing.

16. Method according to claim 1, wherein said body is shaped substantially as a cylinder.

17. Method according to claim 16, wherein said cylinder is hollow.

18. Method according to claim 1, wherein said body is made of material substantially transparent to visible light.

19. Method according to claim 1, wherein said body defines a portion of a preform of a container.

20. Method according to claim 1, wherein said body defines a portion of a container.

21. Method according to claim 2, wherein said obtaining comprises calculating coefficients of said Gabor filter on the basis of said further image.

22. Apparatus comprising:
a light-source for projecting a light and shade pattern defined by preset optic parameters through a body, said light and shade pattern being obtained by a grid having a plurality of parallel stripes, said body having a cylindrical symmetry and a longitudinal axis, said grid being arranged between the light source and the body in such a way that said longitudinal axis is orthogonal with respect to said stripes of said grid, said light and shade pattern comprising a striped pattern, which in turn comprises stripes that are substantially orthogonal to the longitudinal axis of the body;

an image-detecting device for detecting an image of said light and shade pattern through said body to obtain a detected image so that said detected image comprises a plurality of lines, said lines being substantially orthogonal to said longitudinal axis, said body being arranged between said grid and said image detecting device;

a processing device which filters said detected image by means of a Gabor filter for processing said detected image in such a way as to highlight any irregularities of said light and shade pattern in said detected image.

23. Apparatus according to claim 22, wherein said stripes of said plurality of stripes have thicknesses that are substantially the same as one another.

24. Apparatus according to claim 22, wherein said stripes of said plurality of stripes are arranged according to a present pitch.

25. Apparatus according to claim 14, wherein said pitch is substantially constant.

26. Apparatus according to claim 14, wherein said stripes of said plurality of stripes have thicknesses that are substantially the same as one another and said preset optical parameters are correlated to said thickness and to said pitch.

27. Apparatus according to claim 22, wherein said grid is obtained on an emission surface of said light-source.

28. Apparatus according to claim 27, wherein said emission surface is substantially flat.

29. Apparatus according to claim 22, wherein said body is made of material substantially transparent to visible light.

30. Apparatus according to claim 22, wherein said body is shaped substantially as a cylinder.

31. Apparatus according to claim 30, wherein said cylinder is hollow.

32. Apparatus according to claim 22, wherein said body defines a portion of a container preform.

33. Apparatus according to claim 22, wherein said body defines a portion of a container.

34. Apparatus according to claim 22, wherein said image-detecting device comprises a video camera.

35. Apparatus according to claim 34, wherein said grid is obtained on an emission surface of said light-source and said video camera comprises an optical axis substantially orthogonal to said emission surface.

36. Apparatus according to claim 34, wherein said image-detecting device comprises a further video camera, said video camera and said further video camera being oriented in such a way that said first video camera and said second video camera face said body when said body is in a reference position.

37. Apparatus according to claim 22, wherein said processing device is connected to said image-detecting device.

* * * * *